(12) United States Patent
Tsao et al.

(10) Patent No.: US 6,261,546 B1
(45) Date of Patent: Jul. 17, 2001

(54) METHODS AND COMPOSITIONS FOR STABILIZING ACETYLCHOLINE COMPOSITIONS

(75) Inventors: Fu-Pao Tsao, Lawrenceville; George Edward Minno, Suwanee, both of GA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/301,895

(22) Filed: Apr. 29, 1999

Related U.S. Application Data

(60) Provisional application No. 60/150,682, filed on Apr. 29, 1998.

(51) Int. Cl.⁷ .............................. A61K 31/74; A61F 2/14
(52) U.S. Cl. ......................................... 424/78.04; 424/427
(58) Field of Search ................................... 424/78.04, 427

(56) References Cited

U.S. PATENT DOCUMENTS

| | | | |
|---|---|---|---|
| 5,009,892 | 4/1991 | McKinzie | 424/422 |
| 5,565,188 | 10/1996 | Wong | 424/9.411 |
| 5,705,194 | 1/1998 | Wong | 424/489 |

FOREIGN PATENT DOCUMENTS

| | | |
|---|---|---|
| WO 96/32951 | 10/1996 | (WO) . |
| 911264 | 2/1991 | (ZA) . |

OTHER PUBLICATIONS

Solutions Containing Miotic Agents: Effects on Corneal Transendothelial Electrical Potential Difference, Ritsuko Akiyama, et al., Graefe's Arch Cli. Exp. Ophthalmol (1997), 235: 379–383.

*Primary Examiner*—Carlos A Azpuru
(74) *Attorney, Agent, or Firm*—David E. Wildman; Michael U. Lee

(57) ABSTRACT

A pharmaceutical product which includes two-chambers, one having a buffered diluent and the other having acetylcholine. Upon mixing the chamber contents, a buffered efficacious acetylcholine product is prepared for post-surgical ophthlamic injection. Another embodiment of the invention is a method of providing an acetylcholine product which has a substantially consistent final pH without substantial degradation of the acetylcholine. The method involves storing an unbuffered acetylcholine separate from a diluent solution which has been buffered, and mixing prior to use.

19 Claims, 1 Drawing Sheet

METHODS AND COMPOSITIONS FOR STABILIZING ACETYLCHOLINE COMPOSITIONS

This application claims priority under 35 U.S.C. §119(e) to U.S. provisional patent application Ser. No. 60/150,682, which claims priority from U.S. patent application Ser. No. 09/069,552, filed on Apr. 29, 1998.

BACKGROUND OF THE INVENTION

1. Field of the Invention

This invention relates generally to pharmaceutical acetylcholine products. In a preferred embodiment, the invention relates to ophthalmic acetylcholine products.

2. Description of the Related Art

Anterior segment surgery of the eye is relatively common today. These surgical procedures include cataract surgery, penetrating keratoplasty and iridectomy.

Post-surgical treatments are also common. A typical treatment which follows anterior segment surgery involves an immediate application of a pharmaceutical agent which increases the rate of miosis (i.e., constriction of the iris). A preferred miosis-inducing pharmaceutical is acetylcholine, and the chloride salt is the preferred salt. Acetylcholine is also called 2-(acetyloxy)-N,N,N-trimethyl-ethanamium; chloride; acecoline; or arterocoline.

An outstanding product for increasing the miosis rate is sold under the trademark Miochol®-E, which is an intraocular acetylcholine solution marketed by CIBA Vision Corporation, Duluth, Ga. Since aqueous acetylcholine solutions are unstable, the Miochol®-E product is packaged in a vial having two compartments or chambers which are separated from one another by a rubber stopper. The lower chamber contains 20 mg of acetylcholine chloride and 56 mg of mannitol. The upper chamber contains 2 ml of a diluent of sodium chloride, potassium chloride, magnesium chloride hexahydrate, calcium chloride dihydrate and sterile water for injection.

In use, an eye care professional turns a plunger-stopper mechanism a quarter turn and presses to cause the rubber stopper to dislodge and allow diluent from the upper chamber to pass into the lower chamber, thereby mixing the two solutions. The solution is then administered via injection into the anterior chamber (e.g., seconds after a lens has been inserted during cataract surgery), either before or after securing one or more sutures.

SUMMARY OF THE INVENTION

An object of the invention is to increase the stability of an acetylcholine pharmaceutical product.

An object of the invention is to improve the pH consistency of an acetylcholine pharmaceutical product without causing substantial degradation of the acetylcholine.

Another object of the invention is to provide an improved acetylcholine ophthalmic product.

This and other objects and advantages are achieved through the innovative stabilized product which includes two-compartment acetylcholine product. In one compartment, acetylcholine is stored. In a second compartment, a buffered diluent solution is stored. Upon mixing the buffered diluent, a buffered acetylcholine product is prepared for injection.

Another embodiment of the invention is a method of providing an acetylcholine product which has a substantially consistent final pH without substantial degradation of the acetylcholine. The method involves storing an unbuffered acetylcholine separate from a diluent solution which has been buffered, and mixing prior to use.

DESCRIPTION OF THE PREFERRED EMBODIMENTS

Figure 1:
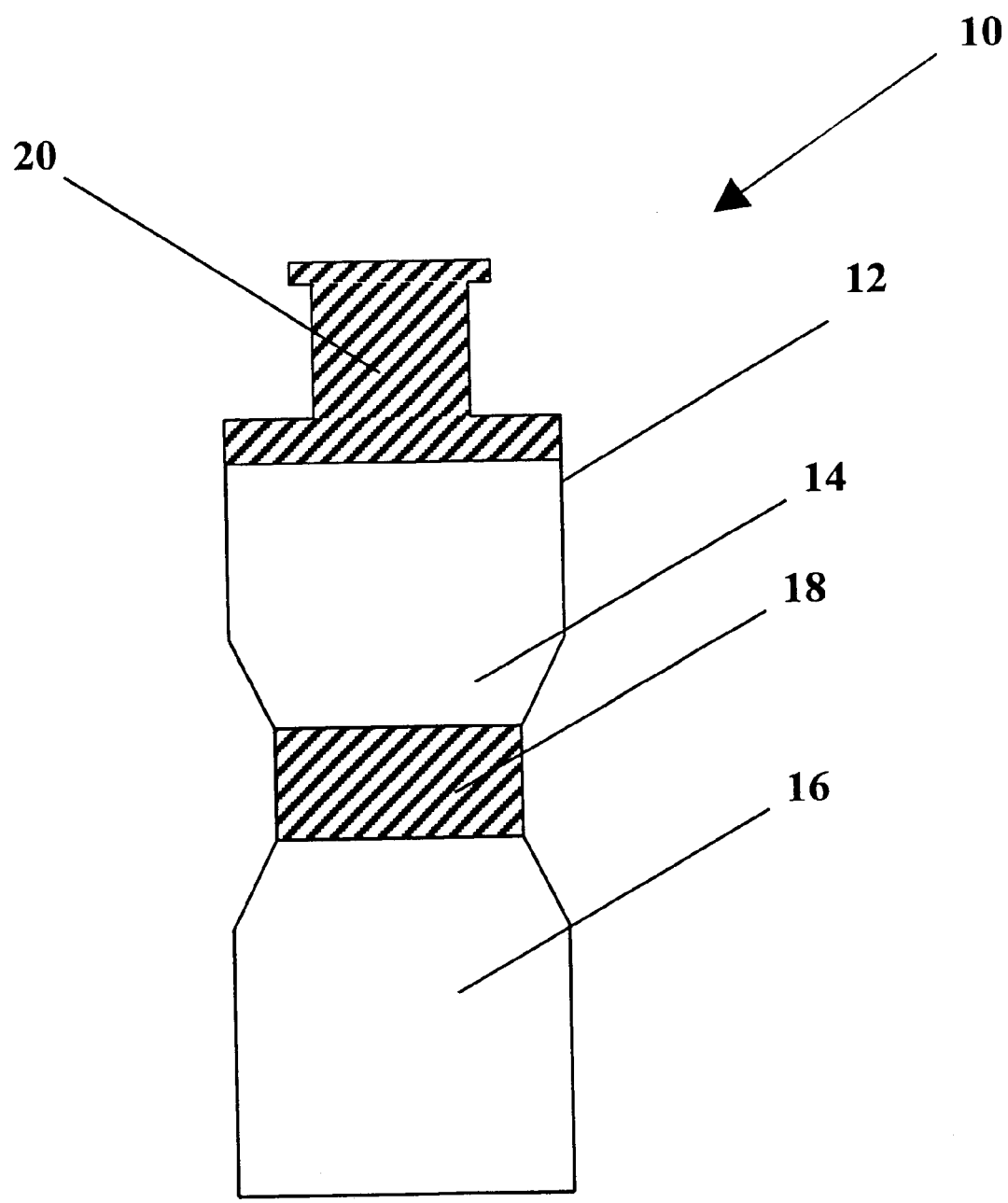
FIG. 1 is a side sectional view of a two-compartment acetylcholine pharmaceutical storage container.

While acetylcholine ophthalmic products have been found to be very effective in post-surgical miosis-inducing treatments, the susceptibility of acetylcholine to degradation or decomposition causes significant manufacturing difficulties. Acetylcholine is similar to a number of other choline esters and related esters of carboxylic acids in that it can easily undergo acid and alkaline catalyzed hydrolyses. Accordingly, the current commercial process of manufacturing acetylcholine involves lyophilization (freeze-drying) and storage of the lyophilized acetylcholine in a separate compartment addresses some of the decomposition concerns.

However, acetylcholine is still susceptible to some decomposition. Due to its hygroscopic nature, minute amounts of water may be adsorbed subsquent to lyophilization and prior to packaging, and this water can catalyze decomposition. While this amount of degradation may not be sufficient to cause efficacy problems in the final product, any decomposition of acetylcholine generates acetic acid. Even minor amounts of degradation causes a substantial shift in final product pH, sometimes sufficient to lower the pH below 5.0. Since the product is injected into the eye, the pH must be maintained at an ophthalmically acceptable level. Accordingly, there exists a need to improve the pH stability or consistency of aqueous acetylcholine products, and the present invention addresses this need.

Acetylcholine is susceptible to decomposition as the pH varies from neutral, either in an acidic or a basic range. Thus, buffering of the acetylcholine composition in its storage chamber would presumably be a method of inhibiting acetylcholine decomposition and associate lower of pH from the acetic acid product. However, quite unexpectedly, it was found that addition of buffer to the acetylcholine chamber actually increased the decomposition rate. While large amounts of buffer could presumably control the final product pH, the buffer cause unacceptable levels of drug decomposition.

In order to remedy the problem, buffer was added to the diluent storage chamber. In this way, only minor decomposition occurs in the acetylcholine-containing chamber. While the pH shifts in the acetylcholine chamber, once the buffered diluent is mixed with the acetylcholine, there is sufficient buffering capacity to bring the pH to an ophthalmically acceptable level. The final solution is utilized shortly after mixing with buffered diluent, so there is not sufficient time for acetylcholine to decompose substantially due to the presence of the buffer.

Hence, in one embodiment, the invention is a pharmaceutical product in a container which includes two chambers. A first chamber retains an aqueous diluent solution comprising at least one buffer. A second chamber retains a pharmaceutically active agent comprising acetylcholine. Upon mixing the solution from the first chamber with the contents of the second chamber, the buffer is present in sufficient quantity to buffer the pH of the mixed solution to an ophthalmically acceptable level. Preferably, the buffer is present in sufficent quantity to buffer the solution above a pH of about 5.0. A preferred upper limit on pH is about 8.2. The acetylcholine chamber is preferably substantially free or entirely free of added buffer.

In another embodiment, the invention is a method of buffering a pharmaceutical product including acetylcholine, comprising the steps of providing a buffered diluent solution in a first container; and providing a substantially unbuffered active solution comprising acetylcholine in a second container. The contents of the containers are mixed prior to use to form a solution having an ophthalmically aceptable pH. Preferably, the buffer is present in sufficient quantity to buffer the pH of the mixed solution above about 5.0.

FIG. 1 illustrates a two-chamber product configuration which is an exemple of a useful product configuration in accordance with the present invention. Ophthalmic product 10 includes container 12 which has first chamber 14 and second chamber 16, positioned such that first chamber 14 is directly over second chamber 16 when container 12 is in a resting position. The chambers are separated by separation means 18, such as a rubber stopper positioned in a narrowed region of container 12. Flexible sealing means 20 provides a removable seal to first chamber 14. First chamber 14 holds a buffered diluent solution. Second chamber 16 holds acetylcholine.

In use, an eye care practitioner may twist and depress sealing means 20 thereby generating pressure which dislodges separation means 18 and allowing diluent solution from first chamber 14 to mix with acetylcholine in second chamber 16.

The first or upper chamber preferably includes salts as tonicity adjustors and for other purposes. A preferred composition of upper chamber includes sodium chloride, potassium chloride, magnesium chloride hexahydrate, calcium chloride dihydrate, at least one buffer and sterile water for injection. The concentration of chloride salts is preferably in the ranges of about 0.005% to 0.10% of each of potassium chloride, magnesium chloride hexahydrate, and calcium chloride dihydrate, based on total final product weight. Particularly preferred concentrations are in the ranges of about 0.04% potassium chloride, about 0.03% magnesium chloride hexahydrate, and about 0.01% calcium chloride dihydrate.

The quantity of diluent in the upper chamber may range somewhat, but is preferably from about 1 to 5 milliliters. A preferred quantity of diluent is about 2 ml.

The buffer may be selected from the group of buffers which can achieve an ophthalmically acceptable pH without generating any other substantial detriment to the composition. Buffers may generally be selected from the group consisting of acetates, borates, phosphates, carbonate, citrates and mixtures thereof Acetates are a preferred group because of the generation of acetic acid when acetylcholine decomposes. A particularly preferred acetate is sodium acetate, and a widely available form is the trihydrate.

The buffer concentration depends upon the buffer selected and the goal of achieving a final product pH which is ophthalmically acceptable. If sodium acetate is chosen as the buffer, the sodium acetate concentration may range from about 0.05 to 0.5, preferably about 0.10 to 0.30 and more preferably about 0.13 to 0.17 weight percent.

The second or lower chamber will include acetylcholine, but may include other additives. For example, the lower chamber preferably includes a tonicity adjustor such as mannitol. However, it is preferred to avoid the presence of buffer with acetylcholine until a time nearing the actual use of the final mixed product, in order to minimize the decomposition rate of acetylcholine. Thus, the lower chamber is preferably substantially or completely free of added buffer.

In one embodiment, the lower chamber includes lyophilized acetylcholine and a tonicity adjustor. Preferably, the lower chamber includes about 0.5 to 5% (5 to 50 mg) of lyophilized acetylcholine and about 1 to 10% (10 to 100 milligrams) of mannitol, based on weight percentages of final product solution. In a preferred embodiment, the lower chamber includes about 2% (20 mg) of lyophilized acetylcholine and about 5.6% (56 mg) of mannitol.

Typically, the mannitol is mixed with the acetylcholine prior to the lyophilization process. Accordingly, the lower chamber preferably includes a cake of lyophilized acetylcholine and mannitol.

The final product characteristics are dictated, at least in part, by ophthalmic compatibility. Thus, the pH and osmolality are those which are ophthalmically compatible. A pH of about 5.0 to 8.2 is a preferred range, while a pH of about 5.5 to 8.0 is more preferred. A preferred osmolality range is about 275 to 330, more preferably about 290 to 310.

The invention has been described in detail, with reference to certain preferred embodiments, in order to enable the reader to practice the invention without undue experimentation. However, a person having ordinary skill in the art will readily recognize that many of the components and parameters may be varied or modified to a certain extent without departing from the scope and spirit of the invention. Furthermore, titles, headings, definitions or the like are provided to enhance the reader's comprehension of this document, and should not be read as limiting the scope of the present invention. Accordingly, the intellectual property rights to this invention are defined only by the following claims and appropriate extensions and equivalents thereof.

That which is claimed is:

1. A pharmaceutical product, comprising a container which includes:
   (a) a first chamber in which is disposed an aqueous diluent solution consisting essentially of water, inorganic salts, and at least one buffer; and
   (b) a second chamber in which is disposed a pharmaceutically active agent comprising acetylcholine,
   wherein, the amount of buffer in the first chamber is sufficient to buffer the pH of a mixed solution resulting from mixture of the aqueous diluent solution and the pharmaceutically active agent to an ophthalmically acceptable level.

2. A pharmaceutical product of claim 1, wherein the pH of the mixed solution is above about 5.0.

3. A pharmaceutical product of claim 1, wherein the buffer is selected from the group consisting of acetates, borates, phosphates, carbonate, citrates and mixtures thereof.

4. A pharmaceutical product of claim 3, wherein the buffer includes at least one acetate.

5. A pharmaceutical product of claim 4, wherein the buffer includes sodium acetate.

6. A pharmaceutical product of claim 5, wherein the sodium acetate is present at a concentration of 0.05 to 0.50 weight percent, based on the total weight of the mixed solution.

7. A pharmaceutical product of claim 1, wherein the aqueous diluent solution disposed in the first chamber consists essentially of:
   (a) potassium chloride;
   (b) magnesium chloride hexahydrate;

(c) calcium chloride dehydrate;
(d) sodium acetate; and
(e) sterile water for injection.

8. A pharmaceutical product of claim 7, wherein the first chamber comprises about 1 to 5 milliliters of a solution comprising:
   (a) about 0.005 to 0.10% potassium chloride;
   (b) about 0.005 to 0.10% magnesium chloride hexahydrate;
   (c) about 0.005 to 0.10% calcium chloride dehydrate;
   (d) about 0.10 to 0.20% sodium acetate; and
   (e) sterile water for injection,
   wherein concentrations are weight percentages based on the total weight of the mixed solution.

9. A pharmaceutical product of claim 1, wherein the pharmaceutically active agent in the second chamber comprises:
   (a) lyophilized acetylcholine; and
   (b) a tonicity adjusting agent.

10. A pharmaceutical product of claim 9, wherein the tonicity adjusting agent includes mannitol.

11. A pharmaceutical product of claim 10, wherein the pharmaceutically active agent in the second chamber comprises:
   (a) about 0.5% to 5% lyophilized acetylcholine; and
   (b) about 1% to 10% of mannitol
   wherein concentrations are weight percentages based on the total weight of the mixed solution.

12. A method for treating an eye following surgery comprising administering a pharmaceutical product of claim 1 following a member selected from the group consisting of cataract surgery, penetrating keratoplasty, and iridectomy.

13. A pharmaceutical product of claim 1, wherein the pharmaceutically active agent disposed within the second chamber is substantially free of buffer.

14. An ophthalmic pharmaceutical product, comprising:
   (a) a first chamber in which is disposed an aqueous diluent solution consisting essentially of:
      (i) about 0.005 to 0.10% potassium chloride;
      (ii) about 0.005 to 0.10% magnesium chloride hexahydrate;
      (iii) about 0.005 to 0.10% calcium chloride dehydrate;
      (iv) about 0.10 to 0.20% sodium acetate; and
      (v) sterile water for injection, and
   (b) a second chamber in which is disposed a pharmaceutically active agent, comprising:
      (i) about 0.5% to 5% lyophilized acetylcholine; and
      (ii) about 1% to 10% of mannitol
   wherein, the amount of buffer in the first chamber is sufficient to buffer the pH of a mixed solution resulting from mixture of the contents of the aqueous diluent solution and the pharmaceutically active agent to above about 5.0, and
   wherein concentrations are weight percentages based on the total weight of the mixed solution.

15. A method of stabilizing a pharmaceutical product comprising acetylcholine, comprising the steps of:
   (a) providing a diluent solution consisting essentially of water, inorganic salts, and at least one buffer in a first container; and
   (b) providing a composition to be dissolved comprising acetylcholine in a second container; and
   (c) mixing the diluent solution from the first container with the composition to be dissolved to form a mixed solution, wherein buffer is present in sufficient quantity in the mixed solution to buffer the pH of the mixed solution to an ophthalmically acceptable pH.

16. A method of claim 15, wherein the first container is affixed to the second container.

17. A method of claim 15, wherein the pH of the mixed solution is above about 5.0.

18. A method of claim 15, wherein the buffer is an acetate.

19. A method of claim 18, wherein the buffer is sodium acetate and the concentration is 0.05 to 0.50 weight percent wherein the concentration is based on the total weight of the mixed solution.

* * * * *

UNITED STATES PATENT AND TRADEMARK OFFICE
CERTIFICATE OF CORRECTION

PATENT NO.     : 6,261,546 B1
DATED          : July 17, 2001
INVENTOR(S)    : Tsao et al.

Page 1 of 1

It is certified that error appears in the above-identified patent and that said Letters Patent is hereby corrected as shown below:

<u>Title page,</u>
Item [56], References Cited, OTHER PUBLICATIONS, add the following reference which was omitted:
-- Comparative Studies on Intraocular Medications, Akira Mimosa et al., Afro-Asian J. Ophthalmol., III/December, pgs. 129-135. --

Item [57], ABSTRACT,
Line 5, change the word "ophthlamic" to -- ophthalmic --.

<u>Column 4,</u>
Line 45, remove the comma which appears after the word "wherein".

<u>Column 5,</u>
Line 1, change "dehydrate" to -- dihydrate --.
Line 10, change "dehydrate" to -- dihydrate --.

<u>Column 6,</u>
Line 4, change "dehydrate" to -- dihydrate --.
Line 11, remove the comma which appears after the word "wherein".

Signed and Sealed this

Eighth Day of October, 2002

*Attest:*

*Attesting Officer*

JAMES E. ROGAN
*Director of the United States Patent and Trademark Office*